United States Patent
Agapiou et al.

(10) Patent No.: US 7,899,573 B2
(45) Date of Patent: Mar. 1, 2011

(54) NON-CONTACT METHOD AND SYSTEM FOR INSPECTING A MULTI-FACETED MACHINE SURFACE

(75) Inventors: John S. Agapiou, Rochester Hills, MI (US); Phillip K Steinacker, Okemos, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 311 days.

(21) Appl. No.: 12/140,051

(22) Filed: Jun. 16, 2008

(65) Prior Publication Data

US 2009/0312863 A1 Dec. 17, 2009

(51) Int. Cl.
*G06F 19/00* (2006.01)
*G01B 7/00* (2006.01)
*G01B 15/00* (2006.01)
*G01N 21/00* (2006.01)
*G06K 9/00* (2006.01)

(52) U.S. Cl. ......... 700/175; 700/159; 700/163; 700/174; 700/180; 700/195; 702/155; 702/182; 702/183; 356/237.1; 356/239.3; 356/239.7; 356/241.1; 382/141; 382/152; 382/154

(58) Field of Classification Search .......... 700/159, 700/163, 174–175, 178, 180, 195; 702/155, 702/182–186; 356/237.1, 239.3, 239.7, 241.1; 382/141, 152, 154
See application file for complete search history.

(56) References Cited

U.S. PATENT DOCUMENTS

| | | | | |
|---|---|---|---|---|
| 4,974,165 A | * | 11/1990 | Locke et al. | 700/193 |
| 5,481,483 A | * | 1/1996 | Ebenstein | 382/152 |
| 6,064,759 A | * | 5/2000 | Buckley et al. | 382/154 |
| 6,690,473 B1 | * | 2/2004 | Stanke et al. | 356/601 |
| 6,967,723 B2 | * | 11/2005 | Bohn et al. | 356/511 |
| 6,970,253 B2 | * | 11/2005 | Lindner et al. | 356/511 |
| 7,209,799 B2 | * | 4/2007 | Agapiou et al. | 700/177 |
| 7,212,291 B2 | * | 5/2007 | De Lega et | 356/512 |
| 7,570,794 B2 | * | 8/2009 | Swanger et al. | 382/141 |
| 2006/0215177 A1 | * | 9/2006 | Doerband | 356/609 |
| 2007/0132990 A1 | * | 6/2007 | Fukami et al. | 356/241.1 |
| 2009/0123032 A1 | * | 5/2009 | Kanisawa et al. | 382/106 |

FOREIGN PATENT DOCUMENTS

| | | |
|---|---|---|
| DE | 101 15 524 A 1 | 11/2001 |
| JP | 7190742 A | 7/1995 |
| JP | 07-286824 A | 10/1995 |
| JP | 10289319 A | 10/1998 |
| JP | 2000-065752 A | 3/2000 |
| JP | 2001124533 A | 5/2001 |
| JP | 3695259 B2 | 9/2005 |

* cited by examiner

Primary Examiner — Ramesh B Patel
(74) Attorney, Agent, or Firm — John A. Miller; Miller IP Group, PLC

(57) ABSTRACT

A system and method for inspecting a machined surface. The method includes acquiring optical information of the machined surface from a predefined orientation. Further, the method includes comparing one or more parameters of the optical information with a corresponding one or more reference parameters. Furthermore, the method includes assessing a quality of the machined surface based on the comparison.

19 Claims, 4 Drawing Sheets

NON-CONTACT METHOD AND SYSTEM FOR INSPECTING A MULTI-FACETED MACHINE SURFACE

BACKGROUND OF THE INVENTION

1. Field of the Invention

This invention relates generally to a system and method for optically inspecting a machined surface and, more particularly, to a system and method for optically inspecting valve seats in a cylinder head of a vehicle.

2. Description of the Related Art

In manufacturing processes for machined parts, the quality and dimensions of machined surfaces are very important with regards to the end use of the parts. For example, in the automotive industry, it is necessary that valve seats in a cylinder head of a vehicle meet certain manufacturing tolerances. As a result, there is a need to inspect the properties of machined surfaces to assess their quality and to identify and eliminate any defective parts. This is necessary so that a part can be rejected, accepted or further machined based on the results of the inspection.

Existing systems for inspecting machined surfaces sometimes employ a coordinate measuring machine (CMM) to measure the geometry, profile, form and other details of a machined surface. The measurement typically takes place at regular intervals of a manufacturing process. The assessment of other surface defects, such as chipping or tooling marks, is typically done manually by visual inspection. This makes such inspections prone to errors due to the limitations of human visual performance. Further, most existing inspection systems are time-consuming. As a result, the inspection cannot be performed for all machined parts on a manufacturing line because of the added cost.

A need therefore arises for systems that can automate inspection processes and reduce the time required for inspection to make it substantially equal to the tact time of a machining line. The method should, thereby, enable online inspection of all machined parts, instead of a representative sample. Also, such automated systems would eliminate any errors due to human visual performance, thus making the inspection process faster and less prone to error.

SUMMARY OF THE INVENTION

In accordance with the teachings of the present invention, a system and method are disclosed for inspecting a machined surface of a part. The method includes acquiring optical information of the machined surface from a predefined orientation. Further, the method includes comparing one or more parameters of the optical information with a corresponding one or more reference parameters. Furthermore, the method includes assessing a quality of the machined surface based on the comparison.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a system and method for optically inspecting a machined surface of a part is merely exemplary in nature, and is in no way intended to limit the invention or its applications or uses. For example, the discussion below refers to optically inspecting a valve seat in a cylinder head. However, as will be appreciated by those skilled in the art, the system and method of the invention will have application for other machined surfaces.

Figure 1:
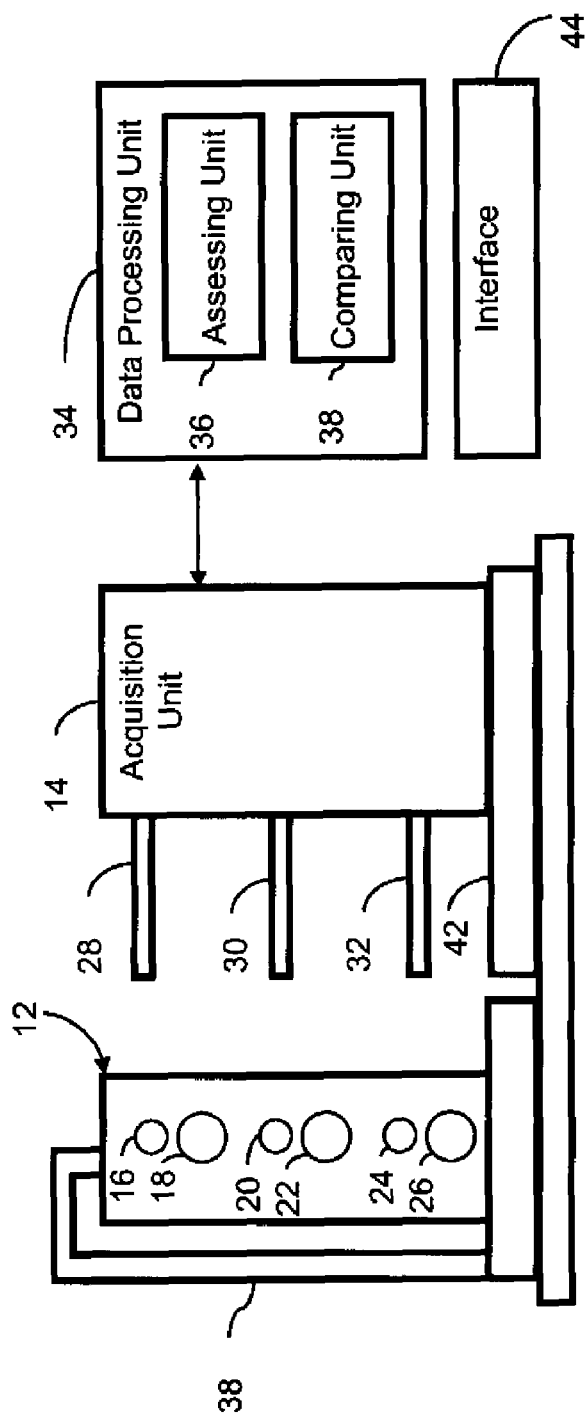
FIG. 1 illustrates a system for inspecting a machined surface, in accordance with an embodiment of the present invention.

FIG. 1 illustrates a system 10 for inspecting one or more machined surfaces of a part 12. In this non-limiting example, the part 12 is a cylinder head for a vehicle including machined valve seats 16, 18, 20, 22, 24 and 26. The system 10 includes an acquisition unit 14 that is capable of acquiring optical information from the machined surfaces, for example, the surfaces of machined valve seats 16, 18, 20, 22, 24 and 26 of the part 12. Examples of the acquisition unit 14 include, but are not limited to, a laser sensor, a digital camera, a line-scan camera with LED lighting and the like. In one embodiment, the acquisition unit 14 can include multiple probes, such that each probe can be used to acquire optical information from a particular machined surface. In this embodiment, the probes can have a laser sensor, a digital camera, a line-scan camera with LED lighting and the like mounted on it, which enable the acquisition of the optical information by the probes. For the purpose of this description, the acquisition unit 14 is shown to include probes 28, 30 and 32. In an exemplary scenario, the probe 28 can be used to acquire information from the machined valve seats 16 and 18. Similarly, the probe 30 can be used to acquire information from the machined valve seats 20 and 22, and the probe 32 can be used to acquire information from the machined valve seats 24 and 26.

In an exemplary embodiment, if a digital camera is used as the acquisition unit 14, the optical information captured is a digital image of the machined surfaces of the part 12. In this case, the digital image is analyzed to facilitate inspection of various parameters representative of the quality of the machined surfaces of the part 12. The parameters include, but are not limited to, a location of one or more elements of the digital image, a linear dimension of the one or more elements of the digital image and an angular dimension of the one or more elements of the digital image. The analysis is done using a data processing unit 34, which includes a comparing unit 38 and an assessing unit 36.

Additional examples of the acquisition unit 14 can be an arrangement of one or more mirrors. In this exemplary embodiment, the optical information can be light reflected from the machined surfaces of the part 12, which is processed to obtain various parameters representative of the machined surface of the part 12. The parameters of the optical information obtained from the aforementioned exemplary case may include the intensity or the width of reflected light.

Although exemplary embodiments have been provided for two types of acquisition units, it will be readily apparent to those with ordinary skill in the art that the invention can be practiced with any of the types of acquisition units, such as those provided in the examples above.

In one embodiment, the system 10 can also include an orientation module 40 to orient the machined surfaces of the part 12 to facilitate acquiring the optical information of the machined surfaces of the part 12.

Further, in an exemplary embodiment, the system can include a movable stage 42 on which the acquisition unit 14 is mounted. This movable stage 42 facilitates the movement of the acquisition unit 14, thereby, providing additional degrees of freedom while acquiring the optical information.

The comparing unit 38 and the assessing unit 36 can operate based on a computer-aided image processing script. The computer-aided image processing script is configured to identify various parameters from the optical information and facilitate comparison of those parameters with reference parameters. The comparing unit 38 compares the parameters obtained from the optical information with reference parameters of the machined surfaces of the part 12. The assessing unit 36, which is operatively connected to the comparing unit 38, assesses the quality of the machined surfaces of the part 12 based on the results of the comparison. The assessment helps in determining if the machined surfaces of the part 12 are fit for further use or need to re-machined or scrapped.

In one embodiment, the system 10 for inspecting one or more machined surfaces of the part 12 can also include an interface 44, which is capable of rendering an output of the system 10, including information related to assessment, statistical information and other related information. Further, the interface 44 can also facilitate input of information into the system 10.

In one exemplary embodiment, the system 10 can be used as a station in a machining line. In this exemplary embodiment, the system 10 receives a manufactured part having a machined surface from a previous station. The manufactured part is oriented to facilitate acquisition of optical information from the machined surface. Thereafter, the optical information is processed, analyzed, and a quality of the surface is assessed. Thereafter, the manufactured part can be transferred to the next station based on the assessed quality. Further, in this exemplary embodiment the orientation, processing, analysis, and assessment of quality can be done in a specific duration of time, which is substantially equal to the tact time of the machining line.

Figure 2:
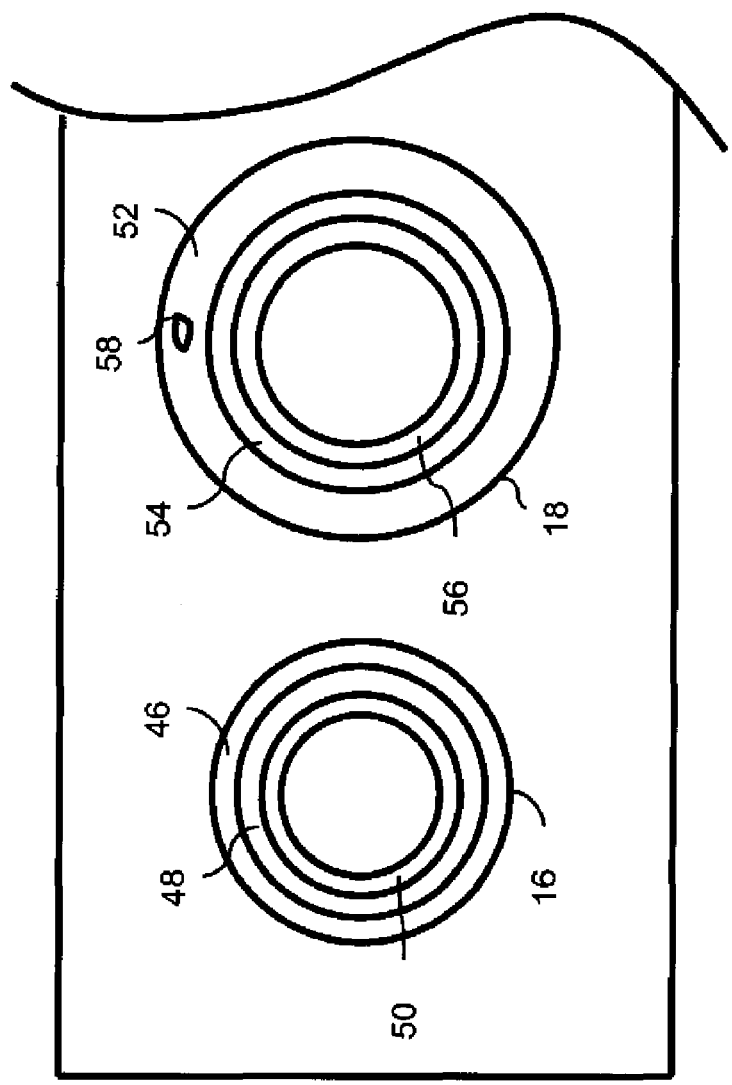
FIG. 2 illustrates an inner face of a cylinder head of an internal combustion (IC) engine, which includes an intake valve seat and an exhaust valve seat forming the machined surface, in accordance with an exemplary embodiment of the present invention.

FIG. 2 illustrates an inner face of the cylinder head part 12 of an internal combustion (IC) engine including the multifaceted cylindrical intake valve seat 16 and the multifaceted cylindrical exhaust valve seat 18 forming machined surfaces, in accordance with an exemplary embodiment of the present invention. Typically, each valve seat in a cylinder head has three surfaces. For the purpose of this description, the intake valve seat 16 is shown to have an intake valve deck land 46, an intake valve seat land 48, and an intake valve throat land 50. Similarly, the exhaust valve seat 18 is shown to include an exhaust valve deck land 52, an exhaust valve seat land 54, and an exhaust valve throat land 56. These are the machined surfaces which require inspection for determining the quality of the cylinder head 12.

The acquisition unit 14 of the system 10 is configured to obtain optical information of the machined surfaces. The optical information is then processed to obtain various parameters representative of the machined surfaces. The information is processed by the comparing unit 38. Some examples of the parameters include, but are not limited to, positional, linear or angular dimensions of elements on the machined surface. For example, a parameter can be the width of the intake valve deck land 46.

In FIG. 2, the exhaust valve seat 18 is shown to include a surface defect 58 on the exhaust valve deck land 52. In an exemplary case, when the acquisition unit 14 is an arrangement of one or more mirrors, as described below, the intensity of the light beam and the width of the light beam are acquired as the optical information. In this exemplary case, the intensity of the light beam reflected from a position corresponding to the surface defect 58 will be different from the reference value of intensity at that position. Therefore, the comparing unit 38 can detect a poor degree of correlation between the acquired intensity and the reference intensity. Accordingly, the assessing unit 14 can identify the surface defect 58 and assess the quality of the surface of exhaust valve deck land 52. Upon detection of such defects, a decision is made as to whether to accept or reject the part. Similarly, a width of the reflected beam can be used to determine the flatness along the width of the lands.

In one embodiment, the magnitudes of reference parameters can be provided in the form of ranges based on pre-specified tolerance limits of the machined surfaces.

Figure 3:
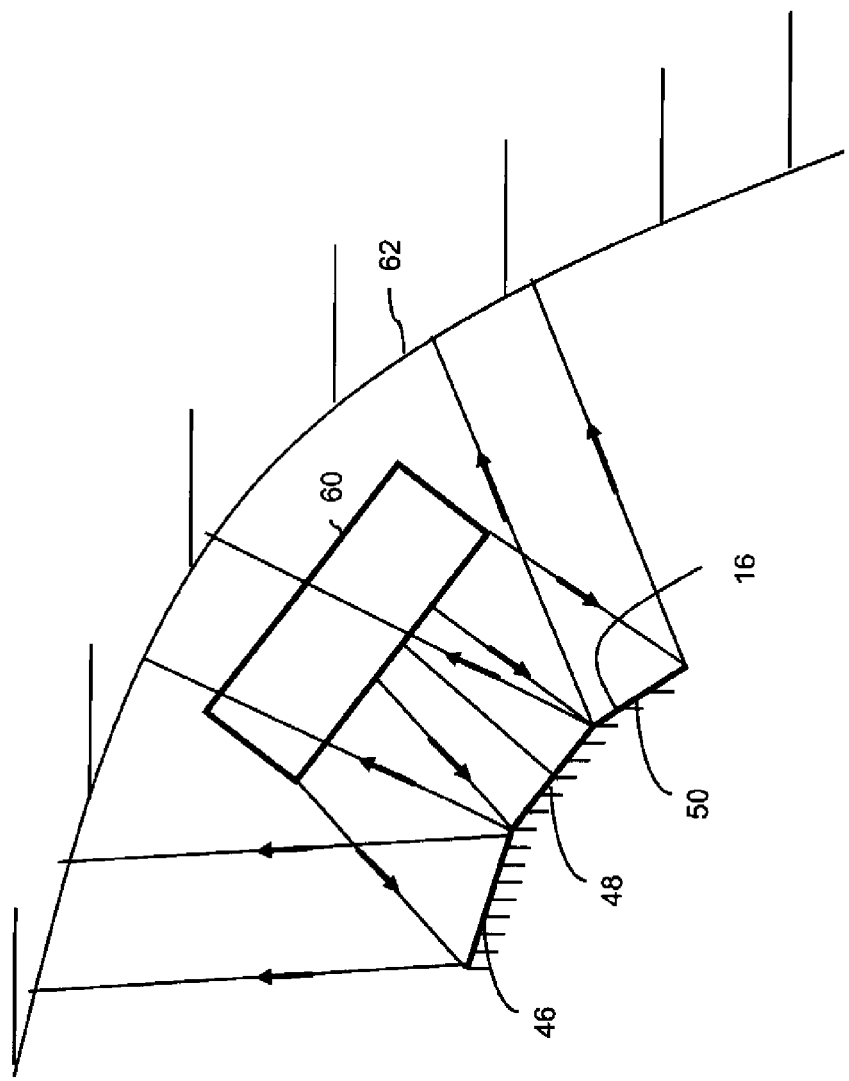
FIG. 3 is an illustration showing an arrangement of a light source and a cylindrical mirror arranged to capture optical information from an intake valve seat.

FIG. 3 is an illustration showing an arrangement of a light source 60 and a cylindrical mirror 62 as an exemplary embodiment of the acquisition unit 14, arranged to capture optical information from an opening for the intake valve seat 16, a portion of whose cross-section is illustrated. Further, FIG. 3 shows the intake valve deck land 46, the intake valve seat land 48, and the intake valve throat land 50 shown in cross-sectional view.

The arrangement is shown to include the cylindrical mirror 62 lying above the light source 60. The light source 60 provides the incident light that hits the machined surfaces and the reflected light gets reflected back to the cylindrical mirror 62. The attributes of the reflected light provide information that is used to assess the machined surfaces. For example, the distance between the reflected light or the position of the reflected light for adjacent segments on the seat 16 determines the angle for each segment. The intensity of the reflected light determines the surface quality, including flatness, of the machined surfaces and the reflected beam width determines the flatness along the width of the lands. The flatness of the surface relates to the waviness of the reflected light. These parameters are then compared against reference parameters of the machined surface to assess whether a particular part will be accepted or rejected.

Although FIG. 2 and FIG. 3 illustrate various embodiments of the present invention with respect to the valve openings of a cylinder head, it will be readily apparent to any person with ordinary skill in the art that the invention can be practiced on other machined surfaces.

Figure 4:
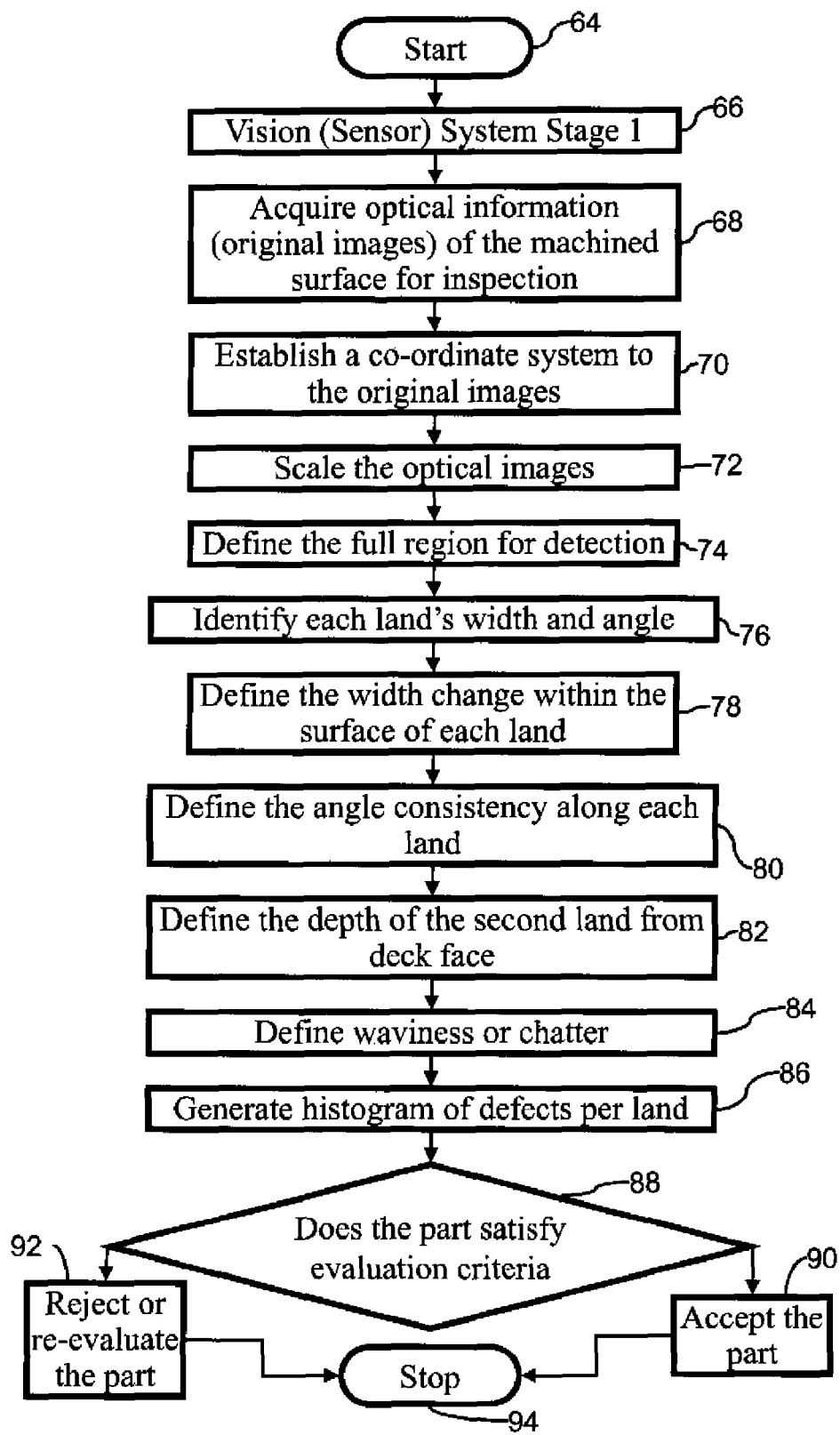
FIG. 4 is a flow diagram illustrating an algorithm of a computer based image processing script used in a non-contact method for inspecting a machined surface, according to an embodiment of the present invention.

FIG. 4 is a flow diagram illustrating an algorithm of a computer based image processing script used in a non-contact method for inspecting a machined surface, according to an embodiment of the present invention. For the purpose of illustration, the machined surface is taken to be the intake valve seat 16 of the cylinder head part 12, which has the intake valve deck land 46, the intake valve seat land 48, and the intake valve throat land 50. The method for inspecting a machined surface is initiated at step 64. At step 66, a vision or sensor system is activated, for example, the acquisition unit 14. Further, for the purpose of illustration, the acquisition unit 14 is explained as a digital camera. At step 68, the optical information of the intake valve seat 16 is acquired. For example, the digital camera acquires the optical information of the intake valve seat 16 in the form of original digital images. At step 70, a coordinate system is established on the acquired digital images. Thereafter, at step 72, the acquired digital images are scaled up or scaled down in size. This is done to substantially match the size of the acquired digital images with the reference images, such that one or more parameters of the acquired digital image can be compared with corresponding reference parameters.

At step 74, the area of interest where the inspection needs to take place is defined. For example, if the intake valve deck land 46 is to be inspected, a region corresponding to the intake valve deck land 46 is defined. At step 76, parameters of the area of interest are identified. For the purpose of illustration, the dimensional parameters may include the width and angle of the intake valve deck land 16. Similar steps can be performed for each land of the intake valve seat 16. At step 78, a change in width on surface of each land is defined. For example, the change in width of the intake valve deck land 46 is ascertained. Similarly, at step 80, a consistency of the angular dimension of the each land is defined. For example, the consistency of the angle of the intake valve deck land 46 is ascertained. Further, at step 82, a depth of a land from a deck is defined. For example, the depth of the intake valve deck land 46 with respect to the intake valve seat land 48 is ascertained. Although, the steps 78, 80 and 82 ascertain change in width, consistency in angle and depth from a deck land, other parameters including intensity or width of light reflected from the surface angle can also be ascertained to inspect the quality of the surface. Thereafter, at step 84, surface properties, such as waviness, chatter along and across each land or a scratch on the surface, is defined based on magnitudes of various parameters as ascertained in the steps 78, 80, and 82. The waviness and chatter can be defined, based on a comparison of the magnitudes of various parameters as ascertained in the steps 78, 80, and 82 with corresponding magnitudes of reference parameters. For example, the waviness and chatter of the intake valve seat land 48 is ascertained.

Thereafter, at step 86 a statistical data based on the outputs of the steps 78, 80, 82 and 84 is generated. For example, the statistical data can be a histogram of the defects per land. At step 88, evaluation criteria are applied to the statistical data to assess a quality of the surface. The evaluation criteria can be applied by comparing the output of the step 86 with corresponding reference values. Thereafter, the part 12 can be accepted at step 90 or rejected at step 92 based on the comparison in step 88.

Thereafter, the method is terminated at step 94.

Various embodiments of the present invention offer one or more advantages. The present invention provides a non-contact method for inspecting a machined surface. The method as per the present invention provides quick inspection of machined surfaces. Further, the present invention can eliminate human intervention while inspection of machined surface, thus improving the accuracy of the inspection method. Furthermore, the present invention enables inspection of machined surfaces of all manufactured parts on a machining line instead of a representative sample. Further inspection of an increased volume of manufactured parts on implementing the present invention, can be used to generate statistical data for various improvement activities of the machining process.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A non-contact method for inspecting a multi-faceted machined surface, the method comprising:
    acquiring optical information for a plurality of facets of the machined surface, wherein the optical information is acquired after reflection of an optical beam from a curved mirror;
    comparing one or more parameters of the optical information with a corresponding one or more reference parameters; and
    assessing the quality of the machined surface based on the comparison.

2. The method according to claim 1 wherein the optical information is acquired by one of a laser sensor, a digital camera, and a line-scan camera with LED lighting.

3. The method according to claim 2 wherein the optical information is a digital image of the machined surface, and wherein the one or more parameters are selected from the group comprising a location of one or more elements of the digital image, a linear dimension of the one or more elements of the digital image and an angular dimension of the one or more elements of the digital image.

4. The method according to claim 1 wherein the one or more parameters are selected from the group comprising an intensity of light reflected from the machined surface and a width of light reflected from the machined surface or parts thereof.

5. The method according to claim 1 wherein comparing one or more parameters includes processing the optical information to determine magnitudes of the one or more parameters and identifying a degree of co-relation between the magnitudes of the one or more parameters and corresponding magnitudes of the one or more reference parameters.

6. The method according to claim 1 wherein comparing one or more parameters is performed based on a computer based image processing script.

7. The method according to claim 1 wherein the facets of the machined surface include a valve seat of a cylinder head of an internal combustion (IC) engine, a valve deck of the cylinder head and a valve throat of the cylinder head.

8. A system for inspecting a multi-faceted machined surface, said system comprising:
    at least one acquisition unit including a cylindrical mirror and being capable of acquiring optical information for a plurality of facets of the machined surface; and
    a data processing unit including at least one comparison unit, said comparison unit being configured to compare the optical information with one or more pre-determined parameters of the machined surface, said data processing unit further including at least one assessing unit configured to assess the quality of the machined surface.

9. The method according to claim 1 wherein assessing the quality of the machined surface comprises identifying defects on the machined surface, and wherein the defects are selected from the group comprising a waviness of the machined surface, a chatter of the machined surface, a scratch on the machined surface and a burr on the machined surface.

10. A non-contact method for inspecting a multi-faceted machined surface, wherein the facets of the machined surface include a valve seat of a cylinder head of an internal combustion (IC) engine, a valve deck of the cylinder head and a valve throat of the cylinder head, the method comprising:
    acquiring optical information for a plurality of facets of the machined surface, wherein the optical information is acquired after reflection of an optical beam from a cylindrical mirror;

identifying one or more parameters of the optical information;

processing the optical information to determine magnitudes of the one or more parameters;

determining a degree of co-relation between the magnitudes of the one or more parameters and corresponding magnitudes of the one or more reference parameters; and assessing the quality of the surface based on the degree of co-relation.

11. The method according to claim 10 wherein the optical information is acquired by one of a laser sensor and a digital camera.

12. The method according to claim 11 wherein the optical information is a digital image of the machined surface, and wherein the one or more parameters are selected from the group comprising a location of one or more elements of the digital image, a linear dimension of the one or more elements of the digital image and an angular dimension of the one or more elements of the digital image.

13. The method according to claim 10 wherein the one or more parameters are selected from the group comprising an intensity of light reflected from the machined surface and a width of light reflected from the machined surface or parts thereof.

14. The method according to claim 10 wherein comparing one or more parameters is performed based on a computer based image processing script.

15. The system according to claim 8 wherein the facets of the machined surface include a valve seat of a cylinder head of an internal combustion (IC) engine, a valve deck of the cylinder head and a valve throat of the cylinder head.

16. The system according to claim 8 wherein the at least one acquisition unit includes a laser sensor or a digital camera.

17. The system according to claim 8 wherein the at least one comparison unit compares the optical information based on a computer-aided image processing script.

18. The system according to claim 8 further comprising an interface to facilitate at least one of an input to the system and render output from the system.

19. The method according to claim 8 wherein the curved mirror is cylindrical in shape.

* * * * *